US008883208B2

(12) United States Patent
McGonigle et al.

(10) Patent No.: US 8,883,208 B2
(45) Date of Patent: Nov. 11, 2014

(54) PARTICLES FOR DELIVERY OF NUCLEIC ACIDS AND RELATED DEVICES AND METHODS

(75) Inventors: Joseph Schmidt McGonigle, Saint Paul, MN (US); Joram Slager, St. Louis Park, MN (US)

(73) Assignee: SurModics, Inc., Eden Prairie, MN (US)

( * ) Notice: Subject to any disclaimer, the term of this patent is extended or adjusted under 35 U.S.C. 154(b) by 429 days.

(21) Appl. No.: 12/756,632

(22) Filed: Apr. 8, 2010

(65) Prior Publication Data
US 2010/0260846 A1 Oct. 14, 2010

Related U.S. Application Data

(60) Provisional application No. 61/167,686, filed on Apr. 8, 2009.

(51) Int. Cl.
| | |
|---|---|
| A61L 27/48 | (2006.01) |
| A61K 9/50 | (2006.01) |
| A61L 17/00 | (2006.01) |
| A61L 29/12 | (2006.01) |
| C12N 15/89 | (2006.01) |
| A61K 9/16 | (2006.01) |
| A61K 48/00 | (2006.01) |
| A61L 31/12 | (2006.01) |
| A61L 17/12 | (2006.01) |
| A61L 27/54 | (2006.01) |
| A61L 31/16 | (2006.01) |
| A61L 29/14 | (2006.01) |
| A61K 9/00 | (2006.01) |

(52) U.S. Cl.
CPC .............. *A61K 9/1641* (2013.01); *A61L 27/48* (2013.01); *A61K 9/5084* (2013.01); *A61L 17/005* (2013.01); *A61L 29/126* (2013.01); *A61L 2300/258* (2013.01); *C12N 15/89* (2013.01); *A61K 9/0024* (2013.01); *A61K 9/1647* (2013.01); *A61K 48/0041* (2013.01); *A61L 31/129* (2013.01); *A61L 2300/62* (2013.01); *A61L 17/12* (2013.01); *A61L 27/54* (2013.01); *A61L 31/16* (2013.01); *A61L 29/148* (2013.01)
USPC ....... 424/484; 424/486; 427/427.4; 514/44 A; 514/44 R

(58) Field of Classification Search
None
See application file for complete search history.

(56) References Cited

U.S. PATENT DOCUMENTS

| | | | |
|---|---|---|---|
| 4,638,045 A | 1/1987 | Kohn et al. | |
| 5,980,948 A | 11/1999 | Goedemoed et al. | |
| 7,910,123 B2 * | 3/2011 | McKay | 424/423 |
| 2003/0133980 A1 | 7/2003 | Costantino et al. | |
| 2005/0255142 A1 | 11/2005 | Chudzik et al. | |
| 2006/0147492 A1 * | 7/2006 | Hunter et al. | 424/426 |
| 2007/0026037 A1 | 2/2007 | Kloke et al. | |
| 2007/0065481 A1 | 3/2007 | Chudzik et al. | |
| 2007/0155906 A1 | 7/2007 | Hissink et al. | |
| 2007/0218102 A1 | 9/2007 | Chudzik et al. | |
| 2007/0224247 A1 | 9/2007 | Chudzik et al. | |
| 2007/0260054 A1 | 11/2007 | Chudzik | |
| 2010/0260850 A1 * | 10/2010 | Slager | 424/487 |

FOREIGN PATENT DOCUMENTS

| | | |
|---|---|---|
| WO | 2007/133812 | 11/2007 |
| WO | 2008/002657 | 1/2008 |
| WO | 2009/091812 | 7/2009 |
| WO | 2009/137689 | 11/2009 |
| WO | 2010/118213 | 10/2010 |
| WO | WO2010118213 | 10/2010 |

OTHER PUBLICATIONS

Perez, C. et al., "Poly(lactic acid)-poly(ethylene glycol) nanoparticles as new carriers for the delivery of plasmid DNA", Journal of Controlled Release Jul. 2001 , vol. 75, Issues 1-2, pp. 211-224.
Aiman, O. "Formulating Poly(Lactide-co-Glycolide) Particles for Plasmid DNA Delivery", Journal of Pharmaceutical Sciences Jul. 2008 , vol. 97, No. 7.
Ambegia, E. "Stabilized plasmid-lipid particles containing PEG-diacylglycerols exhibit extened circulation lifetimes and tumor selective gene expression", Biochimica et Biophysica Acta 2005 , 1669; pp. 155-163.
Blum, Jeremy S. "High loading efficiency and tunable release of plasmid DNA encapsulated in submicron particles fabricated from PLGA conjugated with poly-L-lysine", Journal of Controlled Release 2008 , 129; pp. 66-72.
Nguyen, David N. "Enhancement of poly(orthoester) microspheres for DNA vaccine delivery by blending with poly(ethylenimine)", Biomaterials Jun. 2008 , vol. 29, Issue 18, pp. 2783-2793.
Shinde, R. R. "PEG-PLA/PLGA Nanoparticles for In-Vivo RNAi Delivery", Nanotech 2007 Conference Program 2007 , p. 1 (poster).
Sethuraman et al., "pH-Responsive sulfonamide, PEI system for tumor specific gene delivery: An in vitro study," Biomacromolecules, ACS, Washington, DC, US, vol. 7, No. 1 Dec. 1, 2006, pp. 64-70.

(Continued)

Primary Examiner — Doug Schultz
(74) Attorney, Agent, or Firm — Pauly, DeVries Smith & Deffner, LLC

(57) ABSTRACT

Embodiments of the invention include devices and methods for the release of nucleic acid complexes. In an embodiment the invention includes a nucleic acid delivery particle. The delivery particle can include a polymeric matrix including a polyethyleneglycol containing copolymer and a nucleic acid complex disposed within the polymeric matrix. The nucleic acid complex can include a nucleic acid and a carrier agent. In an embodiment the invention includes a medical device including a first polymeric matrix comprising a first polymer and a plurality of nucleic acid delivery particles disposed within the first polymeric matrix. The medical device can be configured to release the nucleic acid complex when the medical device is implanted within a subject. Other embodiments are included herein.

6 Claims, 3 Drawing Sheets

(56) References Cited

OTHER PUBLICATIONS

Sethuraman et al., "TAT peptide-based micelle system for potential active targeting of anti-cancer agents to acidic solid tumors," Journal of Controlled Release, Elsevier, Amsterdam, NL, vol. 118, No. 2 Mar. 2, 2007, pp. 216-224.

Torchilin, Vladimir P., "Cell penetrating peptide- modified pharmaceutical nanocarriers for intracellular drug and gene delivery," Siopolymers, vol. 90, Jan. 1, 2008, pp. 604-610.

PCT International Search Report and Written Opinion from International Application No. PCT/US2010/030364, corresponding to U.S. Appl. No. 12/756,632, mailed Sep. 5, 2011, pp. 1-16.

PCT Notification Concerning Transmittal of International Preliminary Report on, Patentability from International Application No. PCT/US2010/030364, corresponding to U.S. Appl. No. 12/756,632, mailed Oct. 20, 2011, pp. 1-9.

\* cited by examiner ial Application No. 61/167,686, filed Apr. 8, 2009, the content of which is herein incorporated by reference.

PARTICLES FOR DELIVERY OF NUCLEIC ACIDS AND RELATED DEVICES AND METHODS

This application claims the benefit of U.S. Provisional Application No. 61/167,686, filed Apr. 8, 2009, the content of which is herein incorporated by reference.

FIELD OF THE INVENTION

The present invention relates to devices and methods for the release of active agents. More specifically, the present invention relates to particles for delivery of nucleic acids and related devices and methods for the release of nucleic acid complexes.

REFERENCE TO SEQUENCE LISTING SUBMITTED ELECTRONICALLY VIA EFS-WEB

The content of the electronically submitted sequence listing (Name: 2014_09_04_1001_528_seq_listing_ST25.txt; Size: 1035 bytes; and Date of Creation: Sep. 3, 2014) is incorporated herein by reference in its entirety.

BACKGROUND OF THE INVENTION

One promising approach to the treatment of various medical conditions is the administration of nucleic acids as therapeutic agents. By way of example, this approach can include the administration of RNA, DNA, siRNA, miRNA, piRNA, shRNA, antisense nucleic acids, aptamers, ribozymes, catalytic DNA and the like.

However, for various reasons, successful treatment with nucleic acids can be difficult to achieve. As one example, nucleic acids are readily degraded by enzymes in the in vivo environment.

Accordingly, a need remains for systems and devices that can deliver therapeutic nucleic acids to a target tissue and methods of making and using the same.

SUMMARY OF THE INVENTION

Embodiments of the invention include devices and methods for the delivery of nucleic acids. In an embodiment the invention includes a nucleic acid delivery particle. The delivery particle can include a polymeric matrix including a polyethyleneglycol copolymer and a nucleic acid complex disposed within the polymeric matrix. The nucleic acid complex can include a nucleic acid and a carrier agent.

In an embodiment the invention includes a medical device including a first polymeric matrix comprising a first polymer and a plurality of nucleic acid delivery particles disposed within the first polymeric matrix. Each nucleic acid delivery particle can include a second polymeric matrix comprising a polyethyleneglycol copolymer and a nucleic acid complex disposed within the second polymeric matrix, the nucleic acid complex comprising a nucleic acid and a carrier agent. The medical device can be configured to release the nucleic acid complex when the medical device is implanted within a subject.

In an embodiment the invention can include a method of forming a nucleic acid eluting coating including mixing a plurality of nucleic acid delivery particles, a first polymer, and a solvent to form a coating solution and depositing the coating solution onto a substrate. The nucleic acid delivery particles can include a polymeric matrix including a polyethyleneglycol copolymer and a nucleic acid complex disposed within the polymeric matrix, the nucleic acid complex including a nucleic acid and a carrier agent.

The above summary of the present invention is not intended to describe each discussed embodiment of the present invention. This is the purpose of the figures and the detailed description that follows.

BRIEF DESCRIPTION OF THE FIGURES

The invention may be more completely understood in connection with the following drawings, in which.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

As used herein, the term "complex" shall refer to a chemical association of two or more chemical species through non-covalent bonds.

Embodiments of the invention can include methods for delivering nucleic acids involving disposing the nucleic acids within particles. After the nucleic acid complexes are disposed within particles, they are more robust and less subject to degradation during subsequent processing. Yet the nucleic acid complexes disposed within particles can retain their activity and, as shown in the examples below, can be used successfully to transfect target cells. In some embodiments, the particles can then be incorporated into devices and/or coatings. Aspects of exemplary embodiments will now be described in greater detail.

Figure 1:
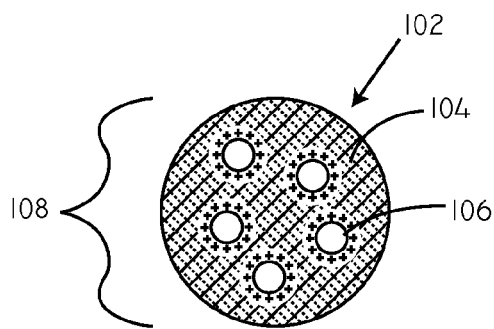
FIG. 1 is a cross-sectional schematic view of a particle including nucleic acid complexes in accordance with an embodiment herein.

Referring now to FIG. 1, a cross-sectional schematic view of a particle 102 including nucleic acid complexes is shown (not to scale). The particle 102 can include a polymeric matrix 104 and one or more nucleic acid complexes 106 within the polymeric matrix 104. The polymer matrix 104 of the particle 102 can include degradable polymers, non-degradable polymers, or a combination of both. In a particular embodiment, the polymeric matrix 104 of the particle can include a polymer in addition to a polyethyleneglycol containing copolymer.

The nucleic acid complexes 106 can include a nucleic acid and a cationic carrier agent. Further details regarding exemplary nucleic acid complexes are provided below. In some embodiments, the particle 102 can have a diameter 108 between about 10 μm and about 120 μm. In some embodiments, the particle 102 can have a diameter 108 between about 50 µm and about 70 µm. In some embodiments, the particle 102 can have a diameter of about 60 µm. In some embodiments, the particle 102 can have a diameter 108 between about 1 µm and about 50 µm. In some embodiments, the particle 102 can have a diameter of less than about 20 µm. In some embodiments, the particle 102 can have a diameter of about 5 µm.

Though the particle 102 shown in FIG. 1 is spherical in cross-section, it will be appreciated that embodiments of the invention can include particles with different shapes including irregular shapes.

Figure 2:
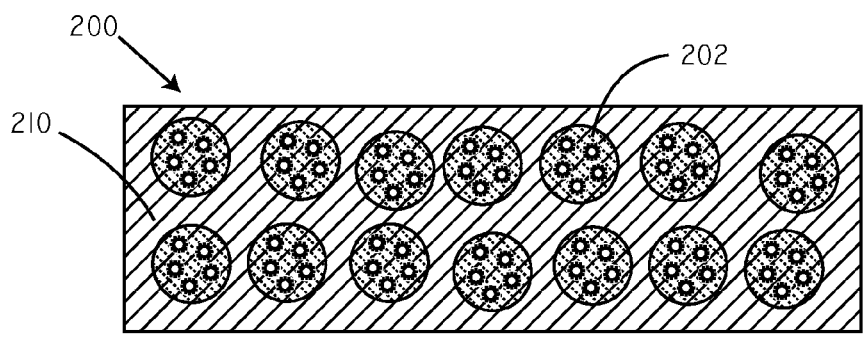
FIG. 2 is a cross-sectional schematic view of an active agent delivery device in accordance with an embodiment herein.

In accordance with various embodiments herein, particles containing nucleic acid complexes can be incorporated within active agent elution control matrices. Referring now to FIG. 2, a plurality of particles 202 are shown disposed within an elution control matrix 210 forming an active agent delivery device 200. The elution control matrix 210 can be made of a material that allows for the elution of the nucleic acid complexes within the particles 202 to the outside of the elution control matrix 210.

The elution control matrix 210 can be composed of various polymers. In some embodiments, the elution control matrix 210 can include degradable polymers. Exemplary degradable polymers are described in greater detail below. In other embodiments, the elution control matrix 210 can include non-degradable polymers. Exemplary non-degradable polymers are described in greater detail below. In some embodiments, the elution control matrix 210 can include both degradable and non-degradable polymers.

In some embodiments, the polymers in the elution control matrix 210 can have solubility properties that are different than the polymers in the particles. In this manner, particles can be mixed in with a solution of polymers used to form the elution control matrix 210, without the particles dissolving. For example, in some embodiments the polymers in the elution control matrix 210 can be water soluble while the polymers in the particle can be soluble in substantially non-polar solvents. Alternatively, the polymers in the elution control matrix 210 can be soluble in substantially non-polar solvents while the polymers in the particle can be water soluble.

The elution control matrix 210 can be deposited using various techniques. By way of example, spray deposition, dip coating, brush coating, printing, casting, and the like. In a particular embodiment, the elution control matrix 210 is deposited from a spray.

In FIG. 2, the active agent delivery device 200 is shown in a substantially planar configuration. However, it will be appreciated that the device 200 can take on many different forms including a filament, a cylinder, an irregular shape, or the like.

Figure 3:
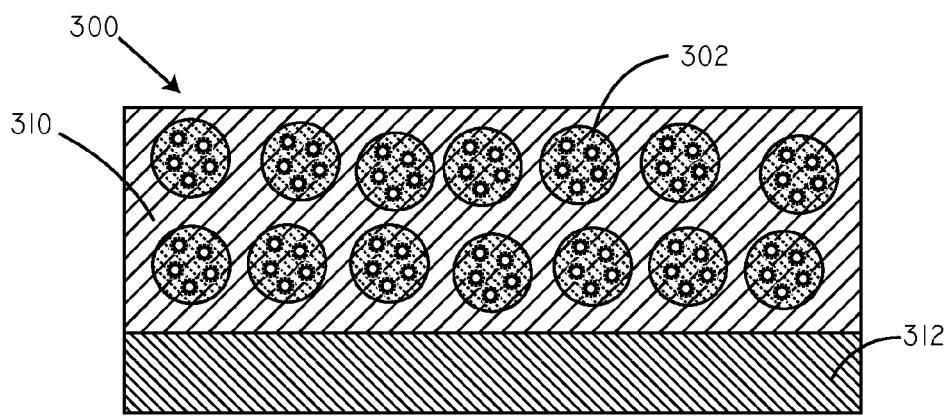
FIG. 3 is a cross-sectional schematic view of an active agent delivery device in accordance with an embodiment herein.

In some embodiments, an elution control matrix including particles containing nucleic acid complexes can be disposed on a substrate, such as on a metal, ceramic, or plastic surface. As an example, such an elution control matrix can be disposed upon a metal stent. Further examples of medical devices included herein are provided below. Referring now to FIG. 3, a device 300 is shown including an elution control matrix 310 with particles 302 including nucleic acid complexes, wherein the elution control matrix 310 is disposed upon a substrate 312. The substrate 312 can include various types of materials including polymers, metals, ceramics, and the like. Further examples of substrate materials are described below. The substrate 312 as illustrated can represent a portion of a medical device.

Nucleic Acids and Nucleic Acid Complexes

Nucleic acids used with embodiments of the invention can include various types of nucleic acids that can function to provide a therapeutic effect. Exemplary types of nucleic acids can include, but are not limited to, ribonucleic acids (RNA), deoxyribonucleic acids (DNA), small interfering RNA (siRNA), micro RNA (miRNA), piwi-interacting RNA (piRNA), short hairpin RNA (shRNA), antisense nucleic acids, aptamers, ribozymes, locked nucleic acids and catalytic DNA.

Nucleic acid complexes used with various embodiments can include a nucleic acid as an active agent and a carrier agent complexed to the nucleic acid. Carrier agents used with embodiments of the invention can include those compounds that can be complexed with nucleic acids in order to preserve the activity of the nucleic acids during the manufacturing and delivery processes. Exemplary classes of suitable carrier agents can include both cationic compounds (compounds having a net positive charge) and charge neutral compounds. By way of example, suitable carrier agents can include cationic and non-cationic polymers and cationic and non-cationic lipids. Exemplary cationic lipids can include, but are not limited to, 3β[N—(N',N'-dimethylaminoethane)-carbamoyl] cholesterol hydrochloride (DC-cholesterol); 1,2-dioleoyl-3-trimethylammonium-propane (DOTAP); dimethyldioctadecylammonium (DDAB); 1,2-dioleoyl-sn-glycero-3-ethylphosphocholine (EPC); 1,2-di-O-octadecenyl-3-trimethylammonium propane (DOTMA); 1,2-di-(9Z-octadecenoyl)-3-dimethylammonium-propane (DODAP); 1,2-dilinoleyloxy-3-dimethylaminopropane (DLinDMA) and derivatives thereof. Exemplary helper or fusogenic lipids can include, but are not limited to, 1,2-dioleoyl-sn-glycero-3-phosphoethanolamine (DOPE); cholesterol; 1,2-dioctadecanoyl-sn-glycero-3-phosphocholine (DSPC); 1,2-distearoyl-sn-glycero-3-phosphoethanolamine (DSPE). Other exemplary lipids can include, but are not limited to, lipidoids, atuplex formulations, and PEGylated forms of lipids described above.

Suitable cationic carrier agents can also include polycation containing cyclodextrin, histones, cationized human serum albumin, aminopolysaccharides such as chitosan, peptides such as poly-L-lysine, poly-L-ornithine, and poly(4-hydroxy-L-proline ester, and polyamines such as polyethylenimine (PEI), polypropylenimine, polyamidoamine dendrimers, and poly(beta-aminoesters). Also included are peptides, such as those that include a nucleic acid binding domain and a nuclear localization domain in order to form a peptide-nucleic acid delivery construct. As used herein, the term "peptide" shall include any compound containing two or more amino-acid residues joined by amide bond(s) formed from the carboxyl group of one amino acid (residue) and the amino group of the next one. As such, peptides can include oligopeptides, polypeptides, proteins, and the like. It will be appreciated that many different peptides are contemplated herein. One exemplary peptide, known as MPG, is a 27 amino acid bipartite amphipathic peptide composed of a hydrophobic domain derived from HIV-1 gp41 protein and a basic domain from the nuclear localization sequence (NLS) of SV40 large T antigen (GALFLGFLGAAGSTMGAWSQPKKKRKV—SEQ ID NO: 1) (commercially available as the N-TER Nanoparticle siRNA Transfection System from Sigma-Aldrich, St. Louis, Mo.). Another exemplary peptide, known as MPGΔ$^{NLS}$, is also a 27 amino acid bipartite amphipathic peptide (GALFLGFLGAAGSTMGAWSQPKSKRKV—SEQ ID NO: 2). Other exemplary peptides can include poly-arginine fusion peptides. Still other exemplary peptides include those with protein transduction domains linked with a double-stranded RNA binding domain.

Other carrier agents can include solid nucleic acid lipid nanoparticles (SNALPs), liposomes, protein transduction domains, polyvinyl pyrrolidone (PVP), peptides (including oligopeptides, polypeptides, proteins), and the like. Additionally, carriers may also be conjugated to molecules which allow them to target specific cell types. Examples of targeting agents include antibodies and peptides which recognize and bind to specific cell surface molecules.

Nucleic acid delivery complexes can be formed from carrier agents and nucleic acids through various processes. In some cases, for example, a cationic carrier agent interacts with an anionic nucleic acid molecule and condenses into a compact, ordered complex. As such, in some embodiments, the nucleic acid can simply be contacted with the carrier agent in order to form nucleic acid delivery complexes.

Degradable Polymers

Degradable polymers can be in conjunction with some embodiments herein. By way of example, in some embodiments degradable polymers can be included in a particle that contains nucleic acid complexes. In some embodiments, degradable polymers can be included in an elution control matrix that includes particles with nucleic acid complexes. Degradable polymers used with embodiments of the invention can include both natural or synthetic polymers. Examples of degradable polymers can include those with hydrolytically unstable linkages in the polymeric backbone. Examples of degradable polymers can also include those subject to enzymatic degradation. Degradable polymers of the invention can include both those with bulk erosion characteristics and those with surface erosion characteristics.

While not intending to be bound by theory, the use of degradable polymers can be advantageous in the context of providing controlled release of nucleic acid complexes because release can be mediated by degradation of the matrix in addition to diffusion through the matrix. In addition, the use of degradable polymers can be advantageous where it allows the whole medical device to be degradable because there is no need to later remove the medical device after implantation.

Synthetic degradable polymers can include: degradable polyesters (such as poly(glycolic acid), poly(lactic acid), poly(lactic-co-glycolic acid), poly(dioxanone), polylactones (e.g., poly(caprolactone)), poly(3-hydroxybutyrate), poly(3-hydroxyvalerate), poly(valerolactone), poly(tartronic acid), poly(β-malonic acid), poly(propylene fumarate)); degradable polyesteramides; degradable polyanhydrides (such as poly(sebacic acid), poly(1,6-bis(carboxyphenoxy)hexane, poly(1,3-bis(carboxyphenoxy)propane); degradable polycarbonates (such as tyrosine-based polycarbonates); degradable polyiminocarbonates; degradable polyarylates (such as tyrosine-based polyarylates); degradable polyorthoesters; degradable polyurethanes; degradable polyphosphazenes; and copolymers thereof.

Specific examples of degradable polymers include poly(ether ester) multiblock copolymers based on poly(ethylene glycol) (PEG) and poly(butylene terephthalate) that can be described by the following general structure:

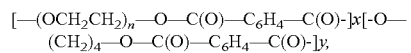

where —$C_6H_4$— designates the divalent aromatic ring residue from each esterified molecule of terephthalic acid, n represents the number of ethylene oxide units in each hydrophilic PEG block, x represents the number of hydrophilic blocks in the copolymer, and y represents the number of hydrophobic blocks in the copolymer. The subscript "n" can be selected such that the molecular weight of the PEG block is between about 300 and about 4000. The block copolymer can be engineered to provide a wide array of physical characteristics (e.g., hydrophilicity, adherence, strength, malleability, degradability, durability, flexibility) and active agent release characteristics (e.g., through controlled polymer degradation and swelling) by varying the values of n, x and y in the copolymer structure. Such degradable polymers can specifically include those described in U.S. Pat. No. 5,980,948, the content of which is herein incorporated by reference in its entirety.

One suitable class of degradable polymers useful in the present invention includes the poly(ether ester) multi-block copolymers. These multi-block copolymers are composed of various pre-polymer building blocks of different combinations of DL-lactide, glycolide, ε-caprolactone and polyethylene glycol. By varying the molecular composition, molecular weight (Mw 1200-6000) and ratio of the pre-polymer blocks, different functionalities can be introduced into the final polymer, which enables the creation of polymers with various physio-chemical properties. Both hydrophobic as well as hydrophilic/swellable polymers and slowly degrading as well as rapidly degrading polymers can be designed.

Exemplary poly(ether ester) multi-block copolymers can include a polymer as shown below:

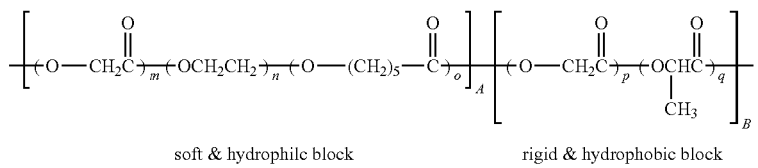

wherein, m and p are each independently glycolide;

n is polyethylene glycol, Mw 300-1000;

o is ε-caprolactone; and q is DL-lactide.

Under physiological conditions, poly(ether ester) multi-block copolymers can degrade completely via hydrolysis into non-toxic degradation products which are metabolized and/or excreted through the urinary pathway. Consequently, there can be no accumulation of biomaterials, thereby minimizing the chance of long-term foreign body reactions.

Additional, features and descriptions of the poly(ether ester) multi-block copolymers are provided, for example, in Published PCT Patent Application No. WO 2005/068533 and references cited therein. An overview is provided below.

The multi-block copolymers can specifically include two hydrolysable segments having a different composition, linked by a multifunctional, specifically an aliphatic chain-extender, and which are specifically essentially completely amorphous under physiological conditions (moist environment, body temperature, which is approximately 37° C. for humans).

The resulting multi-block copolymers can specifically have a structure according to any of the formulae (1)-(3):

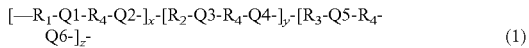

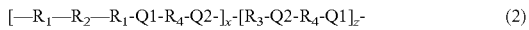

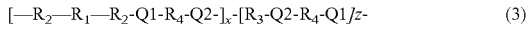

wherein $R_1$ and $R_2$ can be amorphous polyester, amorphous poly ether ester or amorphous polycarbonate; or an amorphous pre-polymer that is obtained from combined ester, ether and/or carbonate groups. $R_1$ and $R_2$ can contain polyether groups, which can result from the use of these compounds as a polymerization initiator, the polyether being amorphous or crystalline at room temperature. However, the polyether thus introduced will become amorphous at physiological conditions. $R_1$ and $R_2$ are derived from amorphous pre-polymers or blocks A and B, respectively, and $R_1$ and $R_2$ are not the same. $R_1$ and $R_2$ can contain a polyether group at the same time. In a specific embodiment, only one of them will contain a polyether group;

z is zero or a positive integer;

$R_3$ is a polyether, such as poly(ethylene glycol), and may be present (z≠0) or not (z=0). $R_3$ will become amorphous under physiological conditions;

$R_4$ is an aliphatic $C_2$-$C_8$ alkylene group, optionally substituted by a $C_1$-$C_{10}$ alkylene, the aliphatic group being linear or cyclic, wherein $R_4$ can specifically be a butylene, —$(CH_2)_4$— group, and the $C_1$-$C_{10}$ alkylene side group can contain protected S, N, P or O moieties;

x and y are both positive integers, which can both specifically be at least 1, whereas the sum of x and y (x+y) can specifically be at most 1000, more specifically at most 500, or at most 100. Q1-Q6 are linking units obtained by the reaction of the pre-polymers with the multifunctional chain-extender. Q1-Q6 are independently amine, urethane, amide, carbonate, ester or anhydride. The event that all linking groups Q are different being rare and not preferred.

Typically, one type of chain-extender can be used with three pre-polymers having the same end-groups, resulting in a copolymer of formula (1) with six similar linking groups. In case pre-polymers $R_1$ and $R_2$ are differently terminated, two types of groups Q will be present: e.g. Q1 and Q2 will be the same between two linked pre-polymer segments $R_1$, but Q1 and Q2 are different when $R_1$ and $R_2$ are linked. When Q1 and Q2 are the same, it means that they are the same type of group but as mirror images of each other.

In copolymers of formula (2) and (3) the groups Q1 and Q2 are the same when two pre-polymers are present that are both terminated with the same end-group (which is usually hydroxyl) but are different when the pre-polymers are differently terminated (e.g. PEG which is diol terminated and a di-acid terminated 'tri-block' pre-polymer). In case of the tri-block pre-polymers ($R_1R_2R_1$ and $R_2R_1R_2$), the outer segments should be essentially free of PEG, because the coupling reaction by ring opening can otherwise not be carried out successfully. Only the inner block can be initiated by a PEG molecule.

The examples of formula (1), (2) and (3) show the result of the reaction with a di-functional chain-extender and di-functional pre-polymers.

With reference to formula (1) the polyesters can also be represented as multi-block or segmented copolymers having a structure (ab)n with alternating a and b segments or a structure (ab)r with a random distribution of segments a and b, wherein 'a' corresponds to the segment $R_1$ derived from pre-polymer (A) and 'b' corresponds to the segment $R_2$ derived from pre-polymer (B) (for z=0). In (ab)r, the a/b ratio (corresponding to x/y in formula (1)) may be unity or away from unity. The pre-polymers can be mixed in any desired amount and can be coupled by a multifunctional chain extender, viz. a compound having at least two functional groups by which it can be used to chemically link the pre-polymers. Specifically, this is a di-functional chain-extender. In case z≠0, then the presentation of a random distribution of all the segments can be given by (abc)r were three different pre-polymers (one being e.g. a polyethylene glycol) are randomly distributed in all possible ratio's. The alternating distribution is given by (abc)r. In this particular case, alternating means that two equally terminated pre-polymers (either a and c or b and c) are alternated with a differently terminated pre-polymer b or a, respectively, in an equivalent amount (a+c=b or b+c=a). Those according to formula (2) or (3) have a structure (aba)n and (bab)n wherein the aba and bab 'triblock' pre-polymers are chain-extended with a di-functional molecule.

The method to obtain a copolymer with a random distribution of a and b (and optionally c) can be more advantageous than when the segments are alternating in the copolymer such as in (ab)n with the ratio of pre-polymers a and b being 1. The composition of the copolymer can then only be determined by adjusting the pre-polymer lengths. In general, the a and b segment lengths in (ab)n alternating copolymers are smaller than blocks in block-copolymers with structures ABA or AB.

The pre-polymers of which the a and b (and optionally c) segments are formed in (ab)r, (abc)r, (ab)n and (abc)n are linked by the di-functional chain-extender. This chain-extender can specifically be a diisocyanate chain-extender, but can also be a diacid or diol compound. In case all pre-polymers contain hydroxyl end-groups, the linking units will be urethane groups. In case (one of) the pre-polymers are carboxylic acid terminated, the linking units are amide groups. Multi-block copolymers with structure (ab)r and (abc)r can also be prepared by reaction of di-carboxylic acid terminated pre-polymers with a diol chain extender or vice versa (diol terminated pre-polymer with diacid chain-extender) using a coupling agent such as DCC (dicyclohexyl carbodiimide) forming ester linkages. In (aba)n and (bab)n the aba and bab pre-polymers are also specifically linked by an aliphatic di-functional chain-extender, more specifically, a diisocyanate chain-extender.

The term "randomly segmented" copolymers refers to copolymers that have a random distribution (i.e. not alternating) of the segments a and b: (ab)r or a, b and c: (abc)r.

Degradable polyesteramides can include those formed from the monomers OH-x-OH, z, and COOH-y-COOH, wherein x is alkyl, y is alkyl, and z is leucine or phenylalanine. Such degradable polyesteramides can specifically include those described in U.S. Pat. No. 6,703,040, the content of which is herein incorporated by reference in its entirety.

Degradable polymeric materials can also be selected from: (a) non-peptide polyamino polymers; (b) polyiminocarbonates; (c) amino acid-derived polycarbonates and polyarylates; and (d) poly(alkylene oxide) polymers.

In an embodiment, the degradable polymeric material is composed of a non-peptide polyamino acid polymer. Exemplary non-peptide polyamino acid polymers are described, for example, in U.S. Pat. No. 4,638,045 ("Non-Peptide Polyamino Acid Bioerodible Polymers," Jan. 20, 1987). Generally speaking, these polymeric materials are derived from monomers, including two or three amino acid units having one of the following two structures illustrated below:

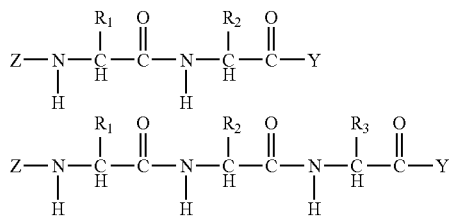

wherein the monomer units are joined via hydrolytically labile bonds at not less than one of the side groups $R_1$, $R_2$, and $R_3$, and where $R_1$, $R_2$, $R_3$ are the side chains of naturally occurring amino acids; Z is any desirable amine protecting group or hydrogen; and Y is any desirable carboxyl protecting group or hydroxyl. Each monomer unit comprises naturally occurring amino acids that are then polymerized as monomer units via linkages other than by the amide or "peptide" bond. The monomer units can be composed of two or three amino acids united through a peptide bond and thus comprise dipeptides or tripeptides. Regardless of the precise composition of the monomer unit, all are polymerized by hydrolytically labile bonds via their respective side chains rather than via the amino and carboxyl groups forming the amide bond typical of polypeptide chains. Such polymer compositions are non-toxic, are degradable, and can provide zero-order release kinetics for the delivery of active agents in a variety of therapeutic applications. According to these aspects, the amino acids are selected from naturally occurring L-alpha amino acids, including alanine, valine, leucine, isoleucine, proline, serine, threonine, aspartic acid, glutamic acid, asparagine, glutamine, lysine, hydroxylysine, arginine, hydroxyproline, methionine, cysteine, cystine, phenylalanine, tyrosine, tryptophan, histidine, citrulline, ornithine, lanthionine, hypoglycin A, β-alanine, γ-amino butyric acid, a aminoadipic acid, canavanine, venkolic acid, thiolhistidine, ergothionine, dihydroxyphenylalanine, and other amino acids well recognized and characterized in protein chemistry.

Natural or naturally-based degradable polymers can include polysaccharides and modified polysaccharides such as starch, cellulose, chitin, chitosan, and copolymers thereof. Hydrophobic derivatives of natural degradable polysaccharide refer to a natural degradable polysaccharide having one or more hydrophobic pendent groups attached to the polysaccharide. In many cases the hydrophobic derivative includes a plurality of groups that include hydrocarbon segments attached to the polysaccharide. When a plurality of groups including hydrocarbon segments are attached, they are collectively referred to as the "hydrophobic portion" of the hydrophobic derivative. The hydrophobic derivatives therefore include a hydrophobic portion and a polysaccharide portion.

The polysaccharide portion includes a natural degradable polysaccharide, which refers to a non-synthetic polysaccharide that is capable of being enzymatically degraded. Natural degradable polysaccharides include polysaccharide and/or polysaccharide derivatives that are obtained from natural sources, such as plants or animals. Natural degradable polysaccharides include any polysaccharide that has been processed or modified from a natural degradable polysaccharide (for example, maltodextrin is a natural degradable polysaccharide that is processed from starch). Exemplary natural degradable polysaccharides include maltodextrin, amylose, cyclodextrin, polyalditol, hyaluronic acid, dextran, heparin, chondroitin sulfate, dermatan sulfate, heparan sulfate, keratan sulfate, dextran, dextran sulfate, pentosan polysulfate, and chitosan. Specific polysaccharides are low molecular weight polymers that have little or no branching, such as those that are derived from and/or found in starch preparations, for example, maltodextrin, amylose, and cyclodextrin. Therefore, the natural degradable polysaccharide can be a substantially non-branched or completely non-branched poly(glucopyranose) polymer.

"Amylose" or "amylose polymer" refers to a linear polymer having repeating glucopyranose units that are joined by α-1,4 linkages. Some amylose polymers can have a very small amount of branching via α-1,6 linkages (about less than 0.5% of the linkages) but still demonstrate the same physical properties as linear (unbranched) amylose polymers do. Generally amylose polymers derived from plant sources have molecular weights of about $1 \times 10^6$ Da or less. Amylopectin, comparatively, is a branched polymer having repeating glucopyranose units that are joined by α-1,4 linkages to form linear portions and the linear portions are linked together via α-1,6 linkages. The branch point linkages are generally greater than 1% of the total linkages and typically 4%-5% of the total linkages. Generally amylopectin derived from plant sources have molecular weights of $1 \times 10^7$ Da or greater.

For example, in some aspects, starch preparations having a high amylose content, purified amylose, synthetically prepared amylose, or enriched amylose preparations can be used in the preparation of a hydrophobic derivative of amylose. In starch sources, amylose is typically present along with amylopectin, which is a branched polysaccharide. If a mixture of amylose and a higher molecular weight precursor is used (such as amylopectin), amylose can be present in the composition in an amount greater than the higher molecular weight precursor. For example, in some aspects, starch preparations having high amylose content, purified amylose, synthetically prepared amylose, or enriched amylose preparations can be used in the preparation of a hydrophobic derivative of amylose polymer. In some embodiments the composition includes a mixture of polysaccharides including amylose wherein the amylose content in the mixture of polysaccharides is 50% or greater, 60% or greater, 70% or greater, 80% or greater, or 85% or greater by weight. In other embodiments the composition includes a mixture of polysaccharides including amylose and amylopectin and wherein the amylopectin content in the mixture of polysaccharides is 30% or less, or 15% or less.

The amount of amylopectin present in a starch may also be reduced by treating the starch with amylopectinase, which cleaves α-1,6 linkages resulting in the debranching of amylopectin into amylose.

Steps may be performed before, during, and/or after the process of derivatizing the amylose polymer with a pendent group comprising a hydrocarbon segment to enrich the amount of amylose, or purify the amylose.

Amylose of particular molecular weights can be obtained commercially or can be prepared. For example, synthetic amyloses with average molecular masses of 70 kDa, 110 kDa, and 320 kDa, can be obtained from Nakano Vinegar Co., Ltd. (Aichi, Japan). The decision of using amylose of a particular size range may depend on factors such as the physical characteristics of the composition (e.g., viscosity), the desired rate of degradation of the implant, and the nature and amount of the active pharmaceutical ingredient (API) or active agent.

Purified or enriched amylose preparations can be obtained commercially or can be prepared using standard biochemical techniques such as chromatography. In some aspects, high-amylose cornstarch can be used to prepare the hydrophobic derivative.

Maltodextrin is typically generated by hydrolyzing a starch slurry with heat-stable α-amylase at temperatures at 85-90° C. until the desired degree of hydrolysis is reached and then inactivating the α-amylase by a second heat treatment. The maltodextrin can be purified by filtration and then spray dried to a final product. Maltodextrins are typically characterized by their dextrose equivalent (DE) value, which is related to the degree of hydrolysis defined as: DE=MW dextrose/number–averaged MW starch hydrolysate×100. Generally, maltodextrins are considered to have molecular weights that are less than amylose molecules.

A starch preparation that has been totally hydrolyzed to dextrose (glucose) has a DE of 100, whereas starch has a DE of about zero. A DE of greater than 0 but less than 100 characterizes the mean-average molecular weight of a starch hydrolysate, and maltodextrins are considered to have a DE of less than 20. Maltodextrins of various molecular weights, for example, in the range of about 500 Da to 5000 Da are commercially available (for example, from CarboMer, San Diego, Calif.).

Another contemplated class of natural degradable polysaccharides is natural degradable non-reducing polysaccharides. A non-reducing polysaccharide can provide an inert matrix thereby improving the stability of active pharmaceutical ingredients (APIs), such as proteins and enzymes. A non-reducing polysaccharide refers to a polymer of non-reducing disaccharides (two monosaccharides linked through their anomeric centers) such as trehalose (α-D-glucopyranosyl α-D-glucopyranoside) and sucrose (β-D-fructofuranosyl α-D-glucopyranoside). An exemplary non-reducing polysaccharide includes polyalditol which is available from GPC (Muscatine, Iowa). In another aspect, the polysaccharide is a glucopyranosyl polymer, such as a polymer that includes repeating (1→3)O-β-D-glucopyranosyl units. Dextran is an α-D-1,6-glucose-linked glucan with side-chains 1-3 linked to the backbone units of the dextran biopolymer. Dextran includes hydroxyl groups at the 2, 3, and 4 positions on the glucopyranose monomeric units. Dextran can be obtained from fermentation of sucrose-containing media by *Leuconostoc mesenteroides* B512F.

Dextran can be obtained in low molecular weight preparations. Enzymes (dextranases) from molds such as *Penicillium* and *Verticillium* have been shown to degrade dextran. Similarly many bacteria produce extracellular dextranases that split dextran into low molecular weight sugars.

Chondroitin sulfate includes the repeating disaccharide units of D-galactosamine and D-glucuronic acid, and typically contains between 15 to 150 of these repeating units. Chondroitinase AC cleaves chondroitin sulfates A and C, and chondroitin.

Hyaluronic acid (HA) is a naturally derived linear polymer that includes alternating β-1,4-glucuronic acid and β-1,3-N-acetyl-D-glucosamine units. HA is the principal glycosaminoglycan in connective tissue fluids. HA can be fragmented in the presence of hyaluronidase.

In many aspects the polysaccharide portion and the hydrophobic portion include the predominant portion of the hydrophobic derivative of the natural degradable polysaccharide. Based on a weight percentage, the polysaccharide portion can be about 25% wt of the hydrophobic derivative or greater, in the range of about 25% to about 75%, in the range of about 30% to about 70%, in the range of about 35% to about 65%, in the range of about 40% to about 60%, or in the range of about 45% to about 55%. Likewise, based on a weight percentage of the overall hydrophobic derivative, the hydrophobic portion can be about 25% wt of the hydrophobic derivative or greater, in the range of about 25% to about 75%, in the range of about 30% to about 70%, in the range of about 35% to about 65%, in the range of about 40% to about 60%, or in the range of about 45% to about 55%. In exemplary aspects, the hydrophobic derivative has approximately 50% of its weight attributable to the polysaccharide portion, and approximately 50% of its weight attributable to its hydrophobic portion.

The hydrophobic derivative has the properties of being insoluble in water. The term for insolubility is a standard term used in the art, and meaning 1 part solute per 10,000 parts or greater solvent. (see, for example, Remington: The Science and Practice of Pharmacy, 20th ed. (2000), Lippincott Williams & Wilkins, Baltimore Md.).

A hydrophobic derivative can be prepared by associating one or more hydrophobic compound(s) with a natural degradable polysaccharide polymer. Methods for preparing hydrophobic derivatives of natural degradable polysaccharides are described herein.

The hydrophobic derivatives of the natural degradable polysaccharides specifically have an average molecular weight of up to about 1,000,000 Da, up to about 300,000 Da or up to about 100,000 Da. Use of these molecular weight derivatives can provide implants with desirable physical and drug-releasing properties. In some aspects the hydrophobic derivatives have a molecular weight of about 250,000 Da or less, about 100,000 Da or less, about 50,000 Da or less, or 25,000 Da or less. Particularly specific size ranges for the natural degradable polysaccharides are in the range of about 2,000 Da to about 20,000 Da, or about 4,000 Da to about 10,000 Da.

The molecular weight of the polymer is more precisely defined as "weight average molecular weight" or $M_w$. $M_w$ is an absolute method of measuring molecular weight and is particularly useful for measuring the molecular weight of a polymer (preparation). Polymer preparations typically include polymers that individually have minor variations in molecular weight. Polymers are molecules that have a relatively high molecular weight and such minor variations within the polymer preparation do not affect the overall properties of the polymer preparation. The $M_w$ can be measured using common techniques, such as light scattering or ultracentrifilgation. Discussion of $M_w$ and other terms used to define the molecular weight of polymer preparations can be found in, for example, Allcock, H. R. and Lampe, F. W. (1990) *Contemporary Polymer Chemistry*; pg 271.

The addition of hydrophobic portion will generally cause an increase in molecular weight of the polysaccharide from its underivatized, starting molecular weight. The amount increase in molecular weight can depend on one or more factors, including the type of polysaccharide derivatized, the level of derivation, and, for example, the type or types of groups attached to the polysaccharide to provide the hydrophobic portion.

In some aspects, the addition of hydrophobic portion causes an increase in molecular weight of the polysaccharide of about 20% or greater, about 50% or greater, about 75% or greater, about 100% or greater, or about 125%, the increase in relation to the underivatized form of the polysaccharide.

As an example, a maltodextrin having a starting weight of about 3000 Da is derivatized to provide pendent hexanoate groups that are coupled to the polysaccharide via ester linkages to provide a degree of substitution (DS) of about 2.5. This provides a hydrophobic polysaccharide having a theoretical molecular weight of about 8400 Da.

In forming the hydrophobic derivative of the natural degradable polysaccharide and as an example, a compound having a hydrocarbon segment can be covalently coupled to one or more portions of the polysaccharide. For example, the compound can be coupled to monomeric units along the length of the polysaccharide. This provides a polysaccharide derivative with one or more pendent groups. Each chemical group includes a hydrocarbon segment. The hydrocarbon segment can constitute all of the pendent chemical group, or the hydrocarbon segment can constitute a portion of the pendent chemical group. For example, a portion of the hydrophobic polysaccharide can have the following structural formula (I):

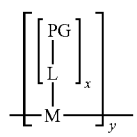

(I)

wherein each M is independently a monosaccharide unit, each L is independently a suitable linking group, or is a direct bond, each PG is independently a pendent group, each x is independently 0 to about 3, such that when x is 0, the bond between L and M is absent, and y is 3 or more.

Additionally, the polysaccharide that includes the unit of formula (I) above can be a compound of the following formula:

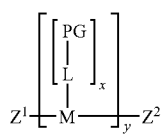

(II)

wherein each M is independently a monosaccharide unit, each L is independently a suitable linking group, or is a direct bond, each PG is independently a pendent group, each x is independently 0 to about 3, such that when x is 0, the bond between L and M is absent, y is about 3 to about 5,000, and $Z^1$ and $Z^2$ are each independently hydrogen, $OR^1$, $OC(=O)R^1$, $CH_2OR^1$, $SiR^1$ or $CH_2OC(=O)R^1$. Each $R^1$ is independently hydrogen, alkyl, cycloalkyl, cycloalkyl alkyl, aryl, aryl alkyl, heterocyclyl or heteroaryl, each alkyl, cycloalkyl, aryl, heterocycle and heteroaryl is optionally substituted, and each alkyl, cycloalkyl and heterocycle is optionally partially unsaturated.

For the compounds of formula (I) and (II), the monosaccharide unit (M) can include D-glucopyranose (e.g., α-D-glucopyranose). Additionally, the monosaccharide unit (M) can include non-macrocyclic poly-α(1→4) glucopyranose, non-macrocyclic poly-α(1→6) glucopyranose, or a mixture or combination of both non-macrocyclic poly-α(1→4) glucopyranose and non-macrocyclic poly-α(1→6) glucopyranose. For example, the monosaccharide unit (M) can include glucopyranose units, wherein at least about 90% are linked by α(1→4) glycosidic bonds. Alternatively, the monosaccharide unit (M) can include glucopyranose units, wherein at least about 90% are linked by α(1→6) glycosidic bonds. Additionally, each of the monosaccharides in the polysaccharide can be the same type (homopolysaccharide), or the monosaccharides in the polysaccharide can differ (heteropolysaccharide).

The polysaccharide can include up to about 5,000 monosaccharide units (i.e., y in the formula (I) or (II) is up to 5,000). Specifically, the monosaccharide units can be glucopyranose units (e.g., α-D-glucopyranose units). Additionally, y in the formula (I) or (II) can specifically be about 3-5,000 or about 3-4,000 or about 100 to 4,000.

In specific embodiments, the polysaccharide is non-macrocyclic. In other specific embodiments, the polysaccharide is linear. In other specific embodiments, the polysaccharide is branched. In yet further specific embodiments, the polysaccharide is a natural polysaccharide (PS).

The polysaccharide will have a suitable glass transition temperature (Tg). In one embodiment, the polysaccharide will have a glass transition temperature (Tg) of at least about 35° C. (e.g., about 40° C. to about 150° C.). In another embodiment, the polysaccharide will have a glass transition temperature (Tg) of –30° C. to about 0° C.

A "pendant group" refers to a group of covalently bonded carbon atoms having the formula $(CH_n)_m$, wherein m is 2 or greater, and n is independently 2 or 1. A hydrocarbon segment can include saturated hydrocarbon groups or unsaturated hydrocarbon groups, and examples thereof include alkyl, alkenyl, alkynyl, cyclic alkyl, cyclic alkenyl, aromatic hydrocarbon and aralkyl groups. Specifically, the pendant group includes linear, straight chain or branched $C_1$-$C_{20}$ alkyl group; an amine terminated hydrocarbon or a hydroxyl terminated hydrocarbon. In another embodiment, the pendant group includes polyesters such as polylactides, polyglycolides, poly(lactide-co-glycolide) co-polymers, polycaprolactone, terpolymers of poly(lactide-co-glycolide-co-caprolactone), or combinations thereof.

The monomeric units of the hydrophobic polysaccharides described herein typically include monomeric units having ring structures with one or more reactive groups. These reactive groups are exemplified by hydroxyl groups, such as the ones that are present on glucopyranose-based monomeric units, e.g., of amylose and maltodextrin. These hydroxyl groups can be reacted with a compound that includes a hydrocarbon segment and a group that is reactive with the hydroxyl group (a hydroxyl-reactive group).

Examples of hydroxyl reactive groups include acetal, carboxyl, anhydride, acid halide, and the like. These groups can be used to form a hydrolytically cleavable covalent bond between the hydrocarbon segment and the polysaccharide backbone. For example, the method can provide a pendent group having a hydrocarbon segment, the pendent group linked to the polysaccharide backbone with a cleavable ester bond. In these aspects, the synthesized hydrophobic derivative of the natural degradable polysaccharide can include chemical linkages that are both enzymatically cleavable (the polymer backbone) and non-enzymatically hydrolytically cleavable (the linkage between the pendent group and the polymer backbone).

Other cleavable chemical linkages (e.g., metabolically cleavable covalent bonds) that can be used to bond the pendent groups to the polysaccharide include carboxylic ester, carbonate, borate, silyl ether, peroxyester groups, disulfide groups, and hydrazone groups. As such, it will be appreciated that degradable polymers herein can include maltodextrin derivatized with silylethers.

In some cases, the hydroxyl reactive groups include those such as isocyanate and epoxy. These groups can be used to form a non-cleavable covalent bond between the pendent group and the polysaccharide backbone. In these aspects, the synthesized hydrophobic derivative of the natural degradable polysaccharide includes chemical linkages that are enzymatically cleavable.

Other reactive groups, such as carboxyl groups, acetyl groups, or sulphate groups, are present on the ring structure of monomeric units of other natural degradable polysaccharides, such as chondroitin or hyaluronic acid. These groups can also be targeted for reaction with a compound having a hydrocarbon segment to be bonded to the polysaccharide backbone.

Various factors can be taken into consideration in the synthesis of the hydrophobic derivative of the natural degradable polysaccharide. These factors include the physical and chemical properties of the natural degradable polysaccharide, including its size, and the number and presence of reactive groups on the polysaccharide and solubility, the physical and chemical properties of the compound that includes the hydrocarbon segment, including its size and solubility, and the reactivity of the compound with the polysaccharide.

In preparing the hydrophobic derivative of the natural degradable polysaccharide any suitable synthesis procedure can be performed. Synthesis can be carried out to provide a desired number of groups with hydrocarbon segments pendent from the polysaccharide backbone. The number and/or density of the pendent groups can be controlled, for example, by controlling the relative concentration of the compound that includes the hydrocarbon segment to the available reactive groups (e.g., hydroxyl groups) on the polysaccharide.

The type and amount of groups having the hydrocarbon segment pendent from the polysaccharide is sufficient for the hydrophobic polysaccharide to be insoluble in water. In order to achieve this, as a general approach, a hydrophobic polysaccharide is obtained or prepared wherein the groups having the hydrocarbon segment pendent from the polysaccharide backbone in an amount in the range of 0.25 (pendent group): 1 (polysaccharide monomer) by weight.

The weight ratio of glucopyranose units to pendent groups can vary, but will typically be about 1:1 to about 100:1. Specifically, the weight ratio of glucopyranose units to pendent groups can be about 1:1 to about 75:1, or about 1:1 to about 50:1. Additionally, the nature and amount of the pendent group can provide a suitable degree of substitution to the polysaccharide. Typically, the degree of substitution will be in the range of about 0.1-5 or about 0.5-2.

To exemplify these levels of derivation, very low molecular weight (less than 10,000 Da) glucopyranose polymers are reacted with compounds having the hydrocarbon segment to provide low molecular weight hydrophobic glucopyranose polymers. In one mode of practice, the natural degradable polysaccharide maltodextrin in an amount of 10 g (MW 3000-5000 Da; ~3 mmols) is dissolved in a suitable solvent, such as tetrahydrofuran. Next, a solution having butyric anhydride in an amount of 18 g (0.11 mols) is added to the maltodextrin solution. The reaction is allowed to proceed, effectively forming pendent butyrate groups on the pyranose rings of the maltodextrin polymer. This level of derivation results in a degree of substitution (DS) of butyrate group of the hydroxyl groups on the maltodextrin of about 1.

For maltodextrin and other polysaccharides that include three hydroxyl groups per monomeric unit, on average, one of the three hydroxyl groups per glycopyranose monomeric unit becomes substituted with a butyrate group. A maltodextrin polymer having this level of substitution is referred to herein as maltodextrin-butyrate DS 1. As described herein, the DS refers to the average number of reactive groups (including hydroxyl and other reactive groups) per monomeric unit that are substituted with pendent groups comprising hydrocarbon segments.

An increase in the DS can be achieved by incrementally increasing the amount of compound that provides the hydrocarbon segment to the polysaccharide. As another example, butyrylated maltodextrin having a DS of 2.5 is prepared by reacting 10 g of maltodextrin (MW 3000-5000 Da; ~3 mmols) with 0.32 mols butyric anhydride.

The degree of substitution can influence the hydrophobic character of the polysaccharide. In turn, implants formed from hydrophobic derivatives having a substantial amount of groups having the hydrocarbon segments bonded to the polysaccharide backbone (as exemplified by a high DS) are generally more hydrophobic and can be more resistant to degradation. For example, an implant formed from maltodextrin-butyrate DS1 has a rate of degradation that is faster than an implant formed from maltodextrin-butyrate DS2.

The type of hydrocarbon segment present in the groups pendent from the polysaccharide backbone can also influence the hydrophobic properties of the polymer. In one aspect, the implant is formed using a hydrophobic polysaccharide having pendent groups with hydrocarbon segments being short chain branched alkyl group. Exemplary short chain branched alkyl group are branched $C_4$-$C_{10}$ groups. The preparation of a hydrophobic polymer with these types of pendent groups is exemplified by the reaction of maltodextrin with valproic acid/anhydride with maltodextrin (MD-val). The reaction can be carried out to provide a relatively lower degree of substitution of the hydroxyl groups, such as is in the range of 0.5-1.5. Although these polysaccharides have a lower degree of substitution, the short chain branched alkyl group imparts considerable hydrophobic properties to the polysaccharide.

Even at these low degrees of substitution the MD-val forms coatings that are very compliant and durable. Because of the low degrees of substitution, the pendent groups with the branched $C_8$ segment can be hydrolyzed from the polysaccharide backbone at a relatively fast rate, thereby providing a degradable coatings that have a relatively fast rate of degradation.

For polysaccharides having hydrolytically cleavable pendent groups that include hydrocarbon segments, penetration by an aqueous solution can promote hydrolysis and loss of groups pendent from the polysaccharide backbone. This can alter the properties of the implant, and can result in greater access to enzymes that promote the degradation of the natural degradable polysaccharide.

Various synthetic schemes can be used for the preparation of a hydrophobic derivative of a natural degradable polysaccharide. In some modes of preparation, pendent polysaccharide hydroxyl groups are reacted with a compound that includes a hydrocarbon segment and a group that is reactive with the hydroxyl groups. This reaction can provide polysaccharide with pendent groups comprising hydrocarbon segments.

Any suitable chemical group can be coupled to the polysaccharide backbone and provide the polysaccharide with hydrophobic properties, wherein the polysaccharide becomes insoluble in water. Specifically, the pendent group can include one or more atoms selected from carbon (C), hydrogen (H), oxygen (O), nitrogen (N), and sulfur (S).

In some aspects, the pendent group includes a hydrocarbon segment that is a linear, branched, or cyclic $C_2$-$C_{18}$ group. More specifically the hydrocarbon segment includes a $C_2$-$C_{10}$, or a $C_4$-$C_8$, linear, branched, or cyclic group. The hydrocarbon segment can be saturated or unsaturated, and can include alkyl groups or aromatic groups, respectively. The hydrocarbon segment can be linked to the polysaccharide chain via a hydrolyzable bond or a non-hydrolyzable bond.

In some aspects the compound having a hydrocarbon segment that is reacted with the polysaccharide backbone is derived from a natural compound. Natural compounds with hydrocarbon segments include fatty acids, fats, oils, waxes, phospholipids, prostaglandins, thromboxanes, leukotrienes, terpenes, steroids, and lipid soluble vitamins.

Exemplary natural compounds with hydrocarbon segments include fatty acids and derivatives thereof, such as fatty acid anhydrides and fatty acid halides. Exemplary fatty acids and anhydrides include acetic, propionic, butyric, isobutyric, valeric, caproic, caprylic, capric, and lauric acids and anhydrides, respectively. The hydroxyl group of a polysaccharide can be reacted with a fatty acid or anhydride to bond the hydrocarbon segment of the compound to the polysaccharide via an ester group.

The hydroxyl group of a polysaccharide can also cause the ring opening of lactones to provide pendent open-chain hydroxy esters. Exemplary lactones that can be reacted with the polysaccharide include caprolactone and glycolides.

Generally, if compounds having large hydrocarbon segments are used for the synthesis of the hydrophobic derivative, a smaller amount of the compound may be needed for its synthesis. For example, as a general rule, if a compound having a hydrocarbon segments with an alkyl chain length of $C_x$ is used to prepare a hydrophobic derivative with a DS of 1, a compound having a hydrocarbon segment with an alkyl chain length of $C_{(x\times2)}$ is reacted in an amount to provide a hydrophobic derivative with a DS of 0.5.

The hydrophobic derivative of the natural degradable polysaccharide can also be synthesized having combinations of pendent groups with two or more different hydrocarbon segments, respectively. For example, the hydrophobic derivative can be synthesized using compounds having hydrocarbon segments with different alkyl chain lengths. In one mode of practice, a polysaccharide is reacted with a mixture of two or more fatty acids (or derivatives thereof) selected from the group of acetic acid, propionic acid, butyric acid, isobutyric acid, valeric acid, caproic acid, caprylic acid, capric acid, and lauric acid to generate the hydrophobic derivative.

In other cases the hydrophobic derivative is synthesized having a non-hydrolyzable bond linking the hydrocarbon segment to the polysaccharide backbone. Exemplary non-hydrolyzable bonds include urethane bonds.

The hydrophobic derivative of the natural degradable polysaccharide can also be synthesized so that hydrocarbon segments are individually linked to the polysaccharide backbone via both hydrolyzable and non-hydrolyzable bonds. As another example, a hydrophobic derivative is prepared by reacting a mixture of butyric acid anhydride and butyl isocyanate with maltodextrin. This yields a hydrophobic derivative of maltodextrin with pendent butyric acid groups that are individually covalently bonded to the maltodextrin backbone with hydrolyzable ester linkages and non-hydrolyzable urethane linkages. The degradation of a coating having this type of hydrophobic derivative can occur by loss of the butyrate groups from hydrolysis of the ester linkages. However, a portion of the butyrate groups (the ones that are bonded via the urethane groups) are not removed from the polysaccharide backbone and therefore the natural degradable polysaccharide can maintain a desired degree of hydrophobicity, prior to enzymatic degradation of the polysaccharide backbone.

In some aspects, the group that is pendent from the polysaccharide includes a hydrocarbon segment that is an aromatic group, such as a phenyl group. As one example, o-acetylsalicylic acid is reacted with a polysaccharide such as maltodextrin to provide pendent chemical group having a hydrocarbon segment that is a phenyl group, and a non-hydrocarbon segment that is an acetate group wherein the pendent group is linked to the polysaccharide via an ester bond.

Degradable polymers of the invention can specifically include polysaccharides such as those described in U.S. Publ. Pat. Application No. 2005/0255142, 2007/0065481, 2007/0218102, 2007/0224247, 2007/0260054, all of which are herein incorporated by reference in their entirety.

Degradable polymers of the invention can further include collagen/hyaluronic acid polymers.

Degradable polymers of the invention can include multi-block copolymers, comprising at least two hydrolysable segments derived from pre-polymers A and B, which segments are linked by a multi-functional chain-extender and are chosen from the pre-polymers A and B, and triblock copolymers ABA and BAB, wherein the multi-block copolymer is amorphous and has one or more glass transition temperatures (Tg) of at most 37° C. (Tg) at physiological (body) conditions. The pre-polymers A and B can be a hydrolysable polyester, polyetherester, polycarbonate, polyestercarbonate, polyanhydride or copolymers thereof, derived from cyclic monomers such as lactide (L,D or L/D), glycolide, ε-caprolactone, δ-valerolactone, trimethylene carbonate, tetramethylene carbonate, 1,5-dioxepane-2-one, 1,4-dioxane-2-one (para-dioxanone) or cyclic anhydrides (oxepane-2,7-dione). The composition of the pre-polymers may be chosen in such a way that the maximum glass transition temperature of the resulting copolymer is below 37° C. at body conditions. To fulfill the requirement of a Tg below 37° C., some of the above-mentioned monomers or combinations of monomers may be more preferred than others. This may by itself lower the Tg, or the pre-polymer is modified with a polyethylene glycol with sufficient molecular weight to lower the glass transition temperature of the copolymer. The degradable multi-block copolymers can include hydrolysable sequences being amorphous and the segments may be linked by a multifunctional chain-extender, the segments having different physical and degradation characteristics. For example, a multi-block co-polyester consisting of a glycolide-ε-caprolactone segment and a lactide-glycolide segment can be composed of two different polyester pre-polymers. By controlling the segment monomer composition, segment ratio and length, a variety of polymers with properties that can easily be tuned can be obtained. Such degradable multi-block copolymers can specifically include those described in U.S. Publ. App. No. 2007/0155906, the content of which is herein incorporated by reference in its entirety.

Non-Degradable Polymers

Non-degradable polymers can be in conjunction with some embodiments herein. By way of example, in some embodiments non-degradable polymers can be included in a particle that contains nucleic acid complexes. In some embodiments, non-degradable polymers can be included in an elution control matrix that includes particles with nucleic acid complexes. In an embodiment, the non-degradable polymer includes a mixture of different polymers. As used herein, the term "(meth)acrylate", when used in describing polymers, shall mean the form including the methyl group (methacrylate) or the form without the methyl group (acrylate).

Non-degradable polymers of the invention can include a polymer selected from the group consisting of poly(alkyl (meth)acrylates) and poly(aromatic(meth)acrylates), where "(meth)" will be understood by those skilled in the art to include such molecules in either the acrylic and/or methacrylic form (corresponding to the acrylates and/or methacrylates, respectively). An exemplary polymer is poly(n-butyl methacrylate) (pBMA). Such polymers are available commercially, e.g., from Aldrich, with molecular weights ranging from about 200,000 Daltons to about 320,000 Daltons, and with varying inherent viscosity, solubility, and form (e.g., as crystals or powder). In some embodiments, poly(n-butyl methacrylate) (pBMA) is used with a molecular weight of about 200,000 Daltons to about 400,000 Daltons.

Examples of suitable polymers also include polymers selected from the group consisting of poly(aryl(meth)acrylates), poly(aralkyl(meth)acrylates), and poly(aryloxyalkyl (meth)acrylates). Such terms are used to describe polymeric structures wherein at least one carbon chain and at least one aromatic ring are combined with acrylic groups, typically esters, to provide a composition. In particular, exemplary polymeric structures include those with aryl groups having from 6 to 16 carbon atoms and with weight average molecular weights from about 50 to about 900 kilodaltons. Suitable poly(aralkyl(meth)acrylates), poly(arylalky(meth)acrylates) or poly(aryloxyalkyl(meth)acrylates) can be made from aromatic esters derived from alcohols also containing aromatic moieties. Examples of poly(aryl(meth)acrylates) include poly(9-anthracenyl methacrylate), poly(chlorophenylacrylate), poly(methacryloxy-2-hydroxybenzophenone), poly(methacryloxybenzotriazole), poly(naphthylacrylate) and -methacrylate), poly(4-nitrophenyl acrylate), poly(pentachloro(bromo, fluoro) acrylate) and -methacrylate), and poly(phenyl acrylate) and -methacrylate). Examples of poly(aralkyl(meth)acrylates) include poly(benzyl acrylate) and -methacrylate), poly(2-phenethyl acrylate) and -methacrylate, and poly(1-pyrenylmethyl methacrylate). Examples of poly(aryloxyalkyl(meth)acrylates) include poly(phenoxyethyl acrylate) and -methacrylate), and poly(polyethylene glycol phenyl ether acrylates) and -methacrylates with varying polyethylene glycol molecular weights.

Examples of suitable polymers also include poly(ethylene-co-vinyl acetate) (pEVA) having vinyl acetate concentrations of between about 10% and about 50% (12%, 14%, 18%, 25%, 33% versions are commercially available), in the form of beads, pellets, granules, etc. The pEVA co-polymers with lower percent vinyl acetate become increasingly insoluble in typical solvents, whereas those with higher percent vinyl acetate become decreasingly durable.

An exemplary polymer mixture includes mixtures of pBMA and pEVA. This mixture of polymers can be used with absolute polymer concentrations (i.e., the total combined concentrations of both polymers in the coating material), of between about 0.25 wt. % and about 99 wt. %. This mixture can also be used with individual polymer concentrations in the coating solution of between about 0.05 wt. % and about 99 wt. %. In one embodiment the polymer mixture includes pBMA with a molecular weight of from 100 kilodaltons to 900 kilodaltons and a pEVA copolymer with a vinyl acetate content of from 24 to 36 weight percent. In an embodiment the polymer mixture includes pBMA with a molecular weight of from 200 kilodaltons to 300 kilodaltons and a pEVA copolymer with a vinyl acetate content of from 24 to 36 weight percent. The concentration of the active agent or agents dissolved or suspended in the coating mixture can range from 0.01 to 99 percent, by weight, based on the weight of the final coating material.

Polymers can also comprise one or more polymers selected from the group consisting of (i) poly(alkylene-co-alkyl(meth) acrylates, (ii) ethylene copolymers with other alkylenes, (iii) polybutenes, (iv) diolefin derived non-aromatic polymers and copolymers, (v) aromatic group-containing copolymers, and (vi) epichlorohydrin-containing polymers.

Poly(alkylene-co-alkyl(meth)acrylates) include those copolymers in which the alkyl groups are either linear or branched, and substituted or unsubstituted with non-interfering groups or atoms. Such alkyl groups can comprise from 1 to 8 carbon atoms, inclusive. Such alkyl groups can comprise from 1 to 4 carbon atoms, inclusive. In an embodiment, the alkyl group is methyl. In some embodiments, copolymers that include such alkyl groups can comprise from about 15% to about 80% (wt) of alkyl acrylate. When the alkyl group is methyl, the polymer contains from about 20% to about 40% methyl acrylate in some embodiments, and from about 25% to about 30% methyl acrylate in a particular embodiment. When the alkyl group is ethyl, the polymer contains from about 15% to about 40% ethyl acrylate in an embodiment, and when the alkyl group is butyl, the polymer contains from about 20% to about 40% butyl acrylate in an embodiment.

Alternatively, polymers can comprise ethylene copolymers with other alkylenes, which in turn, can include straight and branched alkylenes, as well as substituted or unsubstituted alkylenes. Examples include copolymers prepared from alkylenes that comprise from 3 to 8 branched or linear carbon atoms, inclusive. In an embodiment, copolymers prepared from alkylene groups that comprise from 3 to 4 branched or linear carbon atoms, inclusive. In a particular embodiment, copolymers prepared from alkylene groups containing 3 carbon atoms (e.g., propene). By way of example, the other alkylene is a straight chain alkylene (e.g., 1-alkylene). Exemplary copolymers of this type can comprise from about 20% to about 90% (based on moles) of ethylene. In an embodiment, copolymers of this type comprise from about 35% to about 80% (mole) of ethylene. Such copolymers will have a molecular weight of between about 30 kilodaltons to about 500 kilodaltons. Exemplary copolymers are selected from the group consisting of poly(ethylene-co-propylene), poly(ethylene-co-1-butene), poly(ethylene-co-1-butene-co-1-hexene) and/or poly(ethylene-co-1-octene).

"Polybutenes" include polymers derived by homopolymerizing or randomly interpolymerizing isobutylene, 1-butene and/or 2-butene. The polybutene can be a homopolymer of any of the isomers or it can be a copolymer or a terpolymer of any of the monomers in any ratio. As used herein, the term terpolymer shall refer to polymers that include at least three distinct monomers. In an embodiment, the polybutene contains at least about 90% (wt) of isobutylene or 1-butene. In a particular embodiment, the polybutene contains at least about 90% (wt) of isobutylene. The polybutene may contain non-interfering amounts of other ingredients or additives, for instance it can contain up to 1000 ppm of an antioxidant (e.g., 2,6-di-tert-butyl-methylphenol). By way of example, the polybutene can have a molecular weight between about 150 kilodaltons and about 1,000 kilodaltons. In an embodiment, the polybutene can have between about 200 kilodaltons and about 600 kilodaltons. In a particular embodiment, the polybutene can have between about 350 kilodaltons and about 500 kilodaltons. Polybutenes having a molecular weight greater than about 600 kilodaltons, including greater than 1,000 kilodaltons are available but are expected to be more difficult to work with.

Additional alternative polymers include diolefin-derived, non-aromatic polymers and copolymers, including those in which the diolefin monomer used to prepare the polymer or copolymer is selected from butadiene ($CH_2$=CH—CH=$CH_2$) and/or isoprene ($CH_2$=CH—C($CH_3$)=$CH_2$). In an embodiment, the polymer is a homopolymer derived from diolefin monomers or is a copolymer of diolefin monomer with non-aromatic mono-olefin monomer, and optionally, the homopolymer or copolymer can be partially hydrogenated. Such polymers can be selected from the group consisting of polybutadienes prepared by the polymerization of cis-, transand/or 1,2-monomer units, or from a mixture of all three monomers, and polyisoprenes prepared by the polymerization of cis-1,4- and/or trans-1,4-monomer units. Alternatively, the polymer is a copolymer, including graft copolymers, and random copolymers based on a non-aromatic mono-olefin monomer such as acrylonitrile, and an alkyl (meth)acrylate and/or isobutylene. In an embodiment, when the mono-olefin monomer is acrylonitrile, the interpolymerized acrylonitrile is present at up to about 50% by weight; and when the mono-olefin monomer is isobutylene, the diolefin is isoprene (e.g., to form what is commercially known as a "butyl rubber"). Exemplary polymers and copolymers have a molecular weight between about 150 kilodaltons and about 1,000 kilodaltons. In an embodiment, polymers and copolymers have a molecular weight between about 200 kilodaltons and about 600 kilodaltons.

Additional alternative polymers include aromatic group-containing copolymers, including random copolymers, block copolymers and graft copolymers. In an embodiment, the aromatic group is incorporated into the copolymer via the polymerization of styrene. In a particular embodiment, the random copolymer is a copolymer derived from copolymerization of styrene monomer and one or more monomers selected from butadiene, isoprene, acrylonitrile, a $C_1$-$C_4$ alkyl (meth)acrylate (e.g., methyl methacrylate) and/or butene. Useful block copolymers include copolymer containing (a) blocks of polystyrene, (b) blocks of a polyolefin selected from polybutadiene, polyisoprene and/or polybutene (e.g., isobutylene), and (c) optionally a third monomer (e.g., ethylene) copolymerized in the polyolefin block. The aromatic group-containing copolymers contain about 10% to about 50% (wt.) of polymerized aromatic monomer and the molecular weight of the copolymer is from about 300 kilodaltons to about 500 kilodaltons. In an embodiment, the molecular weight of the copolymer is from about 100 kilodaltons to about 300 kilodaltons.

Additional alternative polymers include epichlorohydrin homopolymers and poly(epichlorohydrin-co-alkylene oxide) copolymers. In an embodiment, in the case of the copolymer, the copolymerized alkylene oxide is ethylene oxide. By way of example, epichlorohydrin content of the epichlorohydrin-containing polymer is from about 30% to 100% (wt). In an embodiment, epichlorohydrin content is from about 50% to 100% (wt). In an embodiment, the epichlorohydrin-containing polymers have a molecular weight from about 100 kilodaltons to about 300 kilodaltons.

Non-degradable polymers can also include those described in U.S. Publ. Pat. App. No. 2007/0026037, entitled "DEVICES, ARTICLES, COATINGS, AND METHODS FOR CONTROLLED ACTIVE AGENT RELEASE OR HEMOCOMPATIBILITY", the contents of which are herein incorporated by reference in its entirety. As a specific example, non-degradable polymers can include random copolymers of butyl methacrylate-co-acrylamido-methylpropane sulfonate (BMA-AMPS). In some embodiments, the random copolymer can include AMPS in an amount equal to about 0.5 mol. % to about 40 mol. %.

Polyethyleneglycol Containing Copolymers

Embodiments herein can include the use of polyethyleneglycol containing copolymers (or simply "polyethyleneglycol copolymers"). As used herein, the term "polyethyleneglycol copolymers" shall include block copolymers including polyethylene glycol and one or more different subunit blocks. As such, "polyethyleneglycol copolymers" shall also include terpolymers. It will be appreciated that polyethylene glycol blocks can be polymerized with one or more different hydrophobic or hydrophilic subunit blocks to form polyethyleneglycol copolymers. Specific examples of polyethyleneglycol copolymers include PEG-PBT (polyethyleneglycol-polybutylene terephthalate) copolymers. Exemplary PEG-PBT copolymers can include those described in U.S. Pat. No. 5,980,948, the content of which is herein incorporated by reference in its entirety. However, it will be appreciated that many other subunit blocks can be used to form copolymers with polyethyleneglycol. By way of example, it will be appreciated that many degradable polymers, such as those described above, can be combined with polyethyleneglycol to form polyethyleneglycol containing copolymers. Exemplary subunit blocks can include, but are not limited to, polyvinylpyrrolidone, polylactide, polyglycolide, polylactide-co-glycolide, polycaprolactone, and the like.

Substrates

In accordance with some embodiments herein, a matrix including particles with nucleic acid complexes can be disposed on a substrate. Exemplary substrates can include metals, polymers, ceramics, and natural materials. Substrate polymers include those formed of synthetic polymers, including oligomers, homopolymers, and copolymers resulting from either addition or condensation polymerizations. Examples include, but not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, styrene, vinyl chloride, vinyl acetate, vinyl pyrrolidone, and vinylidene difluoride, condensation polymers including, but are not limited to, polyamides such as polycaprolactam, polylauryl lactam, polyhexamethylene adipamide, and polyhexamethylene dodecanediamide, and also polyurethanes, polycarbonates, polysulfones, poly(ethylene terephthalate), polytetrafluoroethylene, polyethylene, polypropylene, polylactic acid, polyglycolic acid, polysiloxanes (silicones), cellulose, and polyetheretherketone.

Embodiments of the invention can also include the use of ceramics as a substrate. Ceramics include, but are not limited to, silicon nitride, silicon carbide, zirconia, and alumina, as well as glass, silica, and sapphire.

Substrate metals can include, but are not limited to, cobalt, chromium, nickel, titanium, tantalum, iridium, tungsten and alloys such as stainless steel, nitinol or cobalt chromium. Suitable metals can also include the noble metals such as gold, silver, copper, platinum, and alloys including the same.

Certain natural materials can also be used in some embodiments including human tissue, when used as a component of a device, such as bone, cartilage, skin and enamel; and other organic materials such as wood, cellulose, compressed carbon, rubber, silk, wool, and cotton. Substrates can also include carbon fiber. Substrates can also include resins, polysaccharides, silicon, or silica-based materials, glass, films, gels, and membranes.

It will be appreciated that embodiments of the invention can also be used without substrates. By way of example, embodiments can include a matrix with nucleic acid complexes disposed therein in the form of a filament or other shape without including a substrate.

Medical Devices

Embodiments of the invention can include medical devices including particles as described herein. Exemplary medical devices can include a wide range of both implantable devices and non-implantable medical devices. Embodiments of the invention can specifically be used with implantable, or transitorily implantable, devices including, but not limited to, ophthalmic devices configured for placement at an external or internal site of the eye; vascular devices such as grafts, stents, catheters, valves, embolic protection devices, heart assist devices, and the like; surgical devices such as sutures of all types, staples, anastomosis devices, screws, plates, clips, vascular implants, tissue scaffolds; orthopedic devices such as joint implants, acetabular cups, patellar buttons, bone repair/augmentation devices, spinal devices, bone pins, cartilage repair devices, and artificial tendons; dental devices; drug delivery devices such as drug delivery pumps, implanted drug infusion tubes, drug infusion catheters, drug delivery filaments, drug delivery injectable compositions, and intravitreal drug delivery devices; urological devices; respiratory devices; neurological devices; ear nose and throat devices; oncological implants; pain management implants; and the like.

Exemplary medical devices can further include medical implants such as drug delivery depots, mechanical scaffolds, space fillers, filaments, rods, coils, foams. Exemplary medical devices can include both pre-formed and in situ formed devices.

The present invention may be better understood with reference to the following examples. These examples are intended to be representative of specific embodiments of the invention, and are not intended as limiting the scope of the invention.

materials, Birmingham, Ala. "50/50 DLG 4E" refers to a copolymer consisting of 50 mole percent DL-lactide, 50 mole percent glycolide, IV Spec: 0.35-0.45, with an ester end group, obtained from Lakeshore Biomaterials, Birmingham, Ala. "85/15 DLG 2.5E" refers to a copolymer consisting of 85 mole percent DL-lactide, 15 mole percent glycolide, IV Spec: 0.20-0.30, with an ester end group, obtained from Lakeshore Biomaterials, Birmingham, Ala. 1000PEG55PBT45 refers to a copolymer of 55 wt. % polyethylene glycol (molecular weight of 1000 Daltons) and 45 wt. % polybutyleneterephthalate (POLYACTIVE®) obtained from Octoplus, Netherlands.

Briefly, polyplexes including DNA (sample #1-6, 11-12) or siRNA (sample #7-10) in water were mixed with 10 ml dichloromethane (DCM) containing 10% w/w polymer solution (see "Polymer Blend" in Table 1 below). The resulting mixture was homogenized using a mixer for 30 seconds at 18 krpm forming an emulsion. The emulsion was poured into 150 grams 2% w/w PVA solution in distilled deionized water (DDW) that was saturated with 2.8 grams (1.6% w/w) methylene chloride and homogenized at 9.5 krpm (setting 2) for three minutes to form a w/o/w emulsion.

TABLE 1

| Sample | Polyplex | Nucleic Acid Loading | Polymer Blend | Water/Solvent Ratio | Yield (mg) |
|---|---|---|---|---|---|
| 0 | NA | NA | 50/50 DLG 2A | 1:10 | 918.6 |
| 1 | Plasmid DNA/PEI | 1 mg | 50/50 DLG 2A | 1:10 | 454.0 |
| 2 | Plasmid DNA/PEI | 1 mg | 50/50 DLG 2E | 2:10 | 573.7 |
| 3 | Plasmid DNA/PEI | 0.5 mg | 50/50 DLG 2E | 1:10 | 477.4 |
| 4 | Plasmid DNA/PEI | 1 mg | 85/15 DLG 2E | 2:10 | 477.4 |
| 5 | Plasmid DNA/PEI | 0.5 mg | 85/15 DLG 2E | 1:10 | 342.2 |
| 6 | Plasmid DNA/PEI | 1 mg | 20% 1000PEG55P45-80% 50/50DLG2E | 2:10 | 494.6 |
| 7 | siRNA/PEI | 500 ug | 50/50 DLG2E | 1:10 | 582.5 |
| 8 | siRNA/PEI | 500 ug | 50/50 DLG4E | 1:10 | 785.4 |
| 9 | siRNA/PEI | 500 ug | 85/15 DLG2.5E | 1:10 | 338.1 |
| 10 | siRNA/PEI | 500 ug | 20% 1000PEG55P45-80% 50/50DLG2E | 1:10 | 530.4 |
| 11 | DNA/PEI | 2 mg | 25% PEI-75% 50/50 DLG 2A | 400 ul:10 | 9.2 |
| 12 | DNA/PEI | 2 mg | 2.5% PEI-97.5% 50/50 DLG 2A | 400 ul:10 | 676.7 |

EXAMPLES

Example 1

Formation of Microparticles

The amounts of components used and yields obtained for this example are shown below in Table 1. "50/50 DLG 2A" refers to a copolymer consisting of 50 mole percent DL-lactide, 50 mole percent glycolide, IV Spec: 0.15-0.25, with a carboxylic acid end group, obtained from Lakeshore Biomaterials, Birmingham, Ala. "50/50 DLG 2E" refers to a copolymer consisting of 50 mole percent DL-lactide, 50 mole percent glycolide, IV Spec: 0.15-0.25, with an ester end group, obtained from Lakeshore Biomaterials, Birmingham, Ala. "85/15 DLG 2E" refers to a copolymer consisting of 85 mole percent DL-lactide, 15 mole percent glycolide, IV Spec: 0.15-0.25, with an ester end group, obtained from Lakeshore Bio- The w/o/w emulsion was then quickly poured into 1500 ml DDW and stirred for 30 minutes to one hour. The particles were spun at 4200 rpm for 30 minutes and the bulk of the supernatant was discarded.

The particles were then resuspended in the remainder of the supernatant (used sonic bath for several seconds). As a wash step, 1 liter of DDW was then added and the mixture spun at 4200 rpm for 30 minutes. The wash process was repeated three times total. Then the particles were lyophilized.

Particle size was evaluated in water using a Sympatec Helos H2060. The results are shown below in Table 2. Most particles were between 1 and 10 μm with mean particle size on the order of 2 μm. DNA containing particles made using 2 ml of water tended to be larger and more distributed than those made in 1 ml (sample #2, 4, 6). (X10, X50, and X90 respectively describe the particle size upper limit for the $10^{th}$ percentile, $50^{th}$ percentile, and $90^{th}$ percentile of the particle population by mass.)

TABLE 2

| Sample | X10 (μm) | X50 (μm) | X90 (μm) |
| --- | --- | --- | --- |
| 0 | 1.11 | 2.12 | 4.33 |
| 1 | 1.34 | 3.05 | 6.52 |
| 2 | 1.55 | 4.75 | 15.21 |
| 3 | 1.33 | 2.89 | 6.56 |
| 4 | 1.31 | 3.63 | 7.76 |
| 5 | 1.23 | 2.51 | 5.16 |
| 6 | 1.51 | 5.09 | 11.32 |
| 7 | 1.32 | 3.83 | 9.05 |
| 8 | 1.85 | 6.55 | 11.12 |
| 9 | 1.36 | 3.59 | 8.22 |
| 10 | 2.04 | 7.75 | 20.4 |
| 12 | 1.38 | 4.42 | 23.93 |

Example 2

Transfection with Nucleic Acid from Microparticles

Particles as formed in Example 1 above were suspended at 20 mg/ml in complete cell culture media (DMEM+10% FBS+antibiotic/antimycotic). Media containing particles was then added directly to HEK293 cells or incubated at 37° C. for 2, 7, 14 or 28 days. At each time point, particles were pelleted by centrifugation, resuspended in media and then added to cells.

Figure 4:
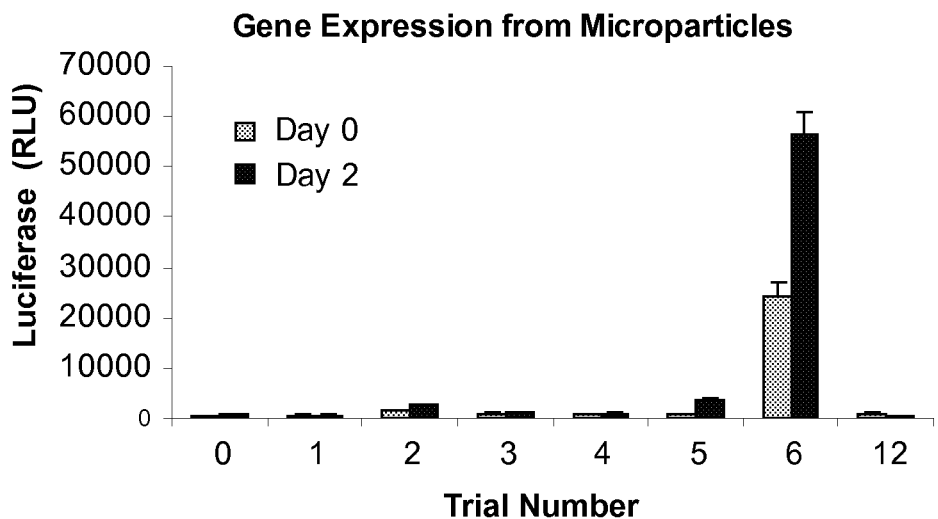
FIG. 4 is a graph of luciferase gene expression over time.
Figure 5:
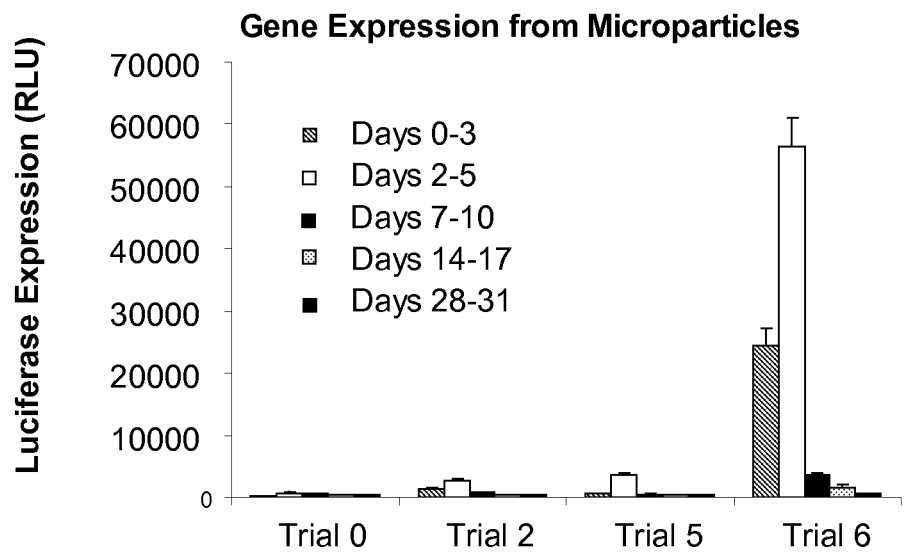
FIG. 5 is a graph of luciferase gene expression over time.

Cells were then incubated with particles for 72-96 hours and assayed for luciferase expression using a luminescence-based detection system. Cells combined with siRNA containing microparticles were observed for fluorescence uptake using an inverted fluorescent microscope. Results for luciferase expression for days 0 and 2 are shown in FIG. 4. FIG. 5 below shows gene expression from sample numbers 0, 2, 5, and 6 as measured over 31 days. Significant levels of gene expression were seen for cells treated with PLGA/1000PEG55PBT45 microparticles. Low levels of gene expression were seen for cells treated with samples 2 and 5 on Day 2. For siRNA-containing microparticles (e.g., samples 7-10), fluorescent uptake was difficult to observe due to interference from the particles.

This example shows that substantial gene expression can be achieved by combining a copolymer of polyethylene glycol along with a degradable polymer.

Example 3

Encapsulation and Release of Peptide/siRNA Complexes

Polymers used were the same as for Example 1 above. Additionally, "85/15 DLCL" refers to a copolymer consisting of 85 mole percent DL-lactide, 15 mole percent caprolactone, obtained from Lakeshore Biomaterials, Birmingham, Ala. The N-TER transfection reagent system was obtained from Sigma, St. Louis, Mo. N-TER (a peptide) was complexed with fluorescein-tagged siRNA as per the manufacturer's protocol and then frozen on dry ice and lyophilized.

Microparticle formulations are listed in Table 3 below. For all formulations 440 μl of 10% w/w polymer solution in dichloromethane was combined with lyophilized siRNA/N-TER complexes containing a total of 40 μg of siRNA and homogenized (IKA 25T, setting '6'). The suspension was emulsified in 15 gr PVA 2% w/w, saturated with dichloromethane (Silverson 5100 rpm, 60 secs) after which it was poured into 150 ml water. The particles were isolated by centrifugation. The supernatants were lyophilized to determine siRNA encapsulation.

The lyophilized supernatants were weighed and reconstituted in HEPES buffer. Non-encapsulated siRNA content was determined by fluorescence. Prior to reading fluorescence, siRNA was decomplexed from N-TER by addition of KDAlert Lysis buffer obtained from Ambion, Austin, Tex.

Figure 6:
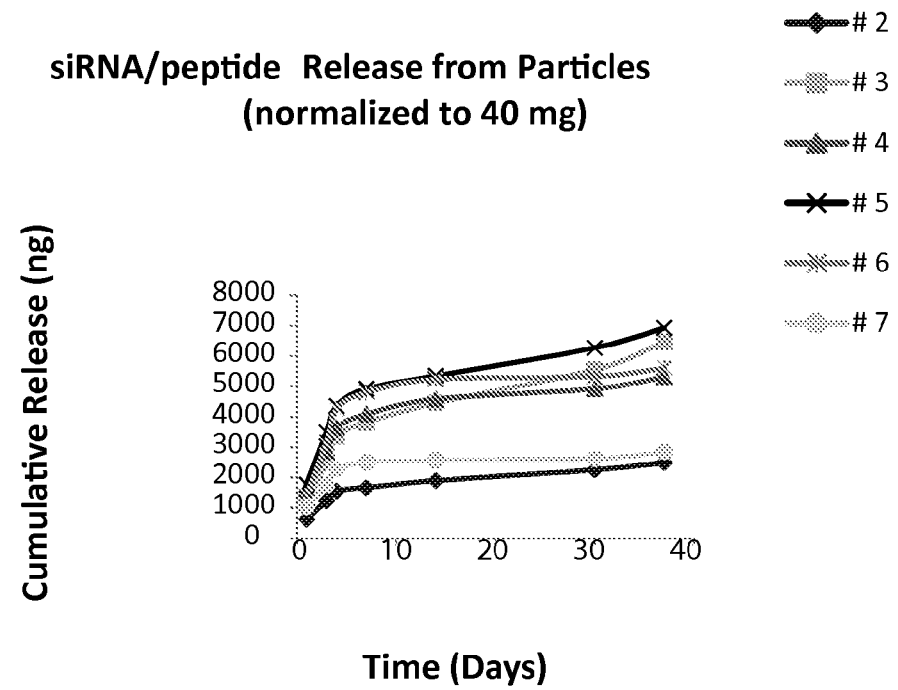
FIG. 6 is a graph of siRNA/peptide release from particles over time.

For controlled release studies 10 mg of each formulation was weighed and put in 500 ul of 10 mM HEPES buffer. The buffer was exchanged at set time points by centrifuging down the particles, removing the supernatant and adding fresh buffer. 100 ul of released sample was added to 100 ul of KDAlert lysis buffer and fluorescence was read to determine the amount of released siRNA. Controlled release results are shown in FIG. 6.

To determine the amount of encapsulated siRNA, 5 mg of microparticles were dissolved in 500 μl of acetonitrile. 500 μl KDAlert lysis buffer was added and the mixture was shaken for 2 hours at 37° C. 100 μl of this extraction was added to a 96 well plate combined with an additional 100 ul KDAlert lysis buffer and fluorescence was read. After the last time point of the controlled release study, remaining siRNA in the particles was analyzed by the same method. The amounts of non-encapsulated siRNA, encapsulated siRNA and released plus remaining siRNA after elution are shown in Table 3.

TABLE 3

| # | Complex | Polymer Blend | Non-Encapsulated siRNA (ug) | Encapsulated siRNA (ug) | Total siRNA Released + Amount Remaining in Particles (ug) |
| --- | --- | --- | --- | --- | --- |
| 1 | None | 85/15 DLCL | 0 | 0 | 0 |
| 2 | N-TER/siRNA | 85/15 DLCL | 3.1 | 11.6 | 11.6 |
| 3 | N-TER/siRNA | 50/50 DLG 2E | 11.7 | 27.3 | 18.2 |
| 4 | N-TER/siRNA | 50/50 DLG 4E | 7.2 | 19.2 | 13.5 |
| 5 | N-TER/siRNA | 20% 1000PEG55P45 80% 85/15DLCL | 3.9 | 27.6 | 23.3 |
| 6 | N-TER/siRNA | 20% 1000PEG55P45 80% 50/50DLG2E | 2.5 | 20.6 | 22.2 |
| 7 | N-TER/siRNA | 20% 1000PEG55P45 80% 50/50DLG4E | 1.7 | 13.8 | 8.3 |

Example 4

Encapsulation and Release of Cationic Lipid/siRNA Complexes

Polymers used were the same as for Example 3 above. 1,2 Dioleoyl-3-trimethylammonium propane (DOTAP) was from Avanti Polar Lipids, Alabaster, Ala. Cholesterol was from Sigma, St. Louis, Mo. Prepared formulations are outlined in Table 4 below. DOTAP/cholesterol was prepared in ethanol at 2.5 mg/ml cholesterol and 22.5 mg/ml DOTAP. 100 µl of DOTAP cholesterol was combined with 250 ug of fluorescein tagged siRNA in 400 µl of $H_2O$. The milky solution was sonicated for 10 mins and then injected into 5 ml 10% w/w polymer solution in dichloromethane and homogenized (IKA 25T, setting '6') for 30 secs. The emulsion was poured into 150 ml PVA 2% w/w saturated with DCM and homogenized for 1 min (Silverson, 5100 rpm). This was then immediately poured into 500 ml DDW and stirred for 20 mins. Particles were isolated by centrifugation and the supernatants were lyophilized.

Figure 7:
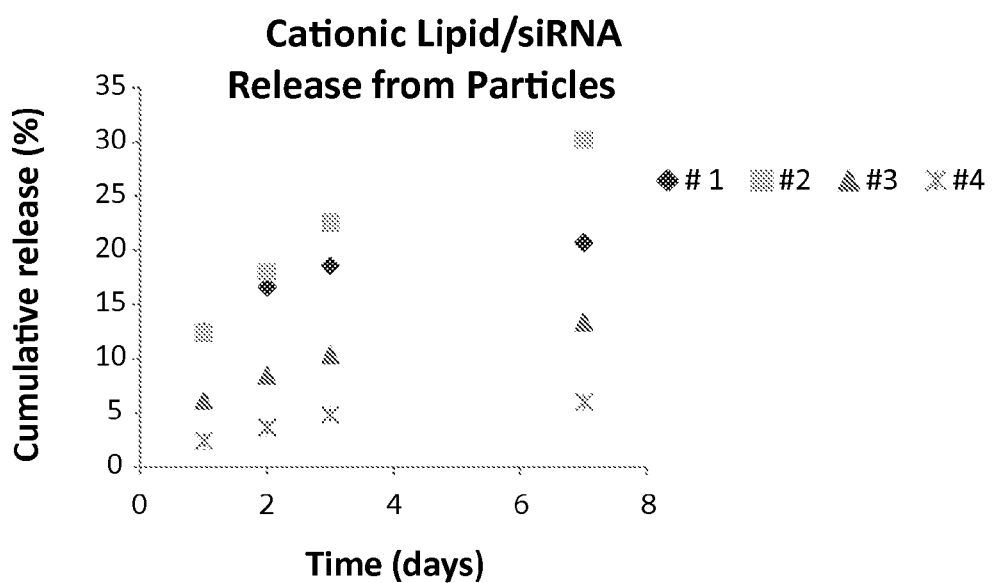
FIG. 7 is a graph of siRNA/cationic lipid release from particles over time.

Release studies and encapsulation measurements were carried out as in Example 3 and results are included in Table 4 and shown in FIG. 7.

TABLE 4

| # | Complex | Polymer Blend | Non-Encapsulated siRNA (ug) | Encapsulated siRNA (ug) | siRNA Released + Amount Remaining in Particles (% of total loading) |
|---|---|---|---|---|---|
| 1 | DOTAP/siRNA | 50/50 DLG 2E | 1.1 | 158 | 46% |
| 2 | DOTAP/siRNA | 50/50 DLG 4E | 0.8 | 273 | 74% |
| 3 | DOTAP/siRNA | 20% 1000PEG55P45 80% 50/50DLG2E | 0.8 | 197 | 39% |
| 4 | DOTAP/siRNA | 20% 1000PEG55P45 80% 50/50DLG4E | 0.9 | 225 | 34% |

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference. Nothing herein is to be construed as an admission that the inventors are not entitled to antedate any publication and/or patent, including any publication and/or patent cited herein.

The invention has been described with reference to various specific and preferred embodiments and techniques. However, it should be understood that many variations and modifications may be made while remaining within the spirit and scope of the invention.

Further Embodiments

In an embodiment the invention includes a nucleic acid delivery particle comprising a polymeric matrix and a nucleic acid complex. The polymeric matrix can include a polyethyleneglycol copolymer. The nucleic acid complex can be disposed within the polymeric matrix and can include a nucleic acid and a carrier agent. The polyethyleneglycol copolymer can include poly(ethyleneglycol-co-butyleneterephthalate) copolymer. In some embodiments the polymeric matrix can include a second polymer. The second polymer can include a degradable polymer. In some embodiments the second polymer can include poly(lactide-co-glycolide) copolymer (PLGA). In some embodiments the second polymer can include polylactide (PLA). In some embodiments the second polymer can include a non-degradable polymer. The carrier agent can include a cationic carrier agent. The carrier agent can include polyethyleneimine. The carrier agent can include a cationic lipid. The carrier agent can include a peptide.

In an embodiment, the medical device can include a medical device including a first polymeric matrix comprising a first polymer; and a plurality of nucleic acid delivery particles disposed within the first polymeric matrix. Each nucleic acid delivery particle can include a second polymeric matrix including a polyethyleneglycol containing copolymer; and a nucleic acid complex disposed within the polymeric matrix, the nucleic acid complex including a nucleic acid and a carrier agent, the medical device configured to release the nucleic acid complex when the medical device is implanted within a subject. In an embodiment, the first polymer can include a water-soluble polymer as applied. In some embodiments, the second polymeric matrix can include a second polymer. In an embodiment, the second polymer can include a non-water-soluble polymer. In an embodiment, the first polymer can be soluble in a solvent for which the second polymer is not. In an embodiment, the second polymer includes a degradable polymer. In an embodiment, the second polymer includes poly (lactide-co-glycolide) copolymer (PLGA). In an embodiment, the second polymer includes polylactide (PLA). In an embodiment, the carrier agent includes a cationic carrier agent. In an embodiment, the carrier agent includes polyethyleneimine. In an embodiment, the carrier agent includes a cationic lipid. In an embodiment, the carrier agent includes a peptide. In an embodiment, the medical device includes a substrate, the first polymeric matrix disposed on the substrate.

In an embodiment, the invention includes a method of forming a nucleic acid eluting coating including mixing a plurality of nucleic acid delivery particles, a first polymer, and a solvent to form a coating solution; and depositing the coating solution onto a substrate. The nucleic acid delivery particles can include a polymeric matrix comprising a polyethyleneglycol containing copolymer; and a nucleic acid complex disposed within the polymeric matrix, the nucleic acid complex comprising a nucleic acid and a cationic carrier agent. In an embodiment, the first polymer is water-soluble. In an embodiment, depositing the coating solution onto the substrate includes spraying the coating solution onto the substrate.

The invention claimed is:

1. A medical device comprising:
   (A) a surface;
   (B) a controlled release coating disposed on the surface of the medical device, the controlled release coating comprising a first polymeric matrix comprising a first polymer having a first solubility; and
   (C) a plurality of nucleic acid delivery microparticles disposed within the controlled release coating, each nucleic acid delivery particle comprising:
   (i) a second polymeric matrix comprising a blend of a polyethyleneglycol copolymer having a second solubility and a degradable polyester; and
   (ii) a nucleic acid complex encapsulated within the second polymeric matrix to form the nucleic acid delivery microparticle, the nucleic acid complex comprising a nucleic acid and a carrier agent, the carrier agent comprising a peptide having a nucleic acid binding domain and a nuclear localization domain;
   wherein the first polymer matrix comprises polymers that are soluble in a non-polar solvent and the second polymer matrix comprises polymers soluble in a polar solvent.

2. The medical device of claim 1, the polyethyleneglycol copolymer comprising poly(ethyleneglycol-co-butyleneterephthalate).

3. The medical device of claim 1, the first polymer comprising a degradable polymer.

4. The medical device of claim 1, the degradable polyester comprising poly(lactide-co-glycolide) copolymer (PLGA).

5. The medical device of claim 1, the nucleic acid selected from the group consisting of plasmid DNA and siRNA.

6. The medical device of claim 1, the first polymer comprising a hydrophobic polysaccharide.

* * * * *

SEQUENCE LISTING

```
<160> NUMBER OF SEQ ID NOS: 2

<210> SEQ ID NO 1
<211> LENGTH: 27
<212> TYPE: PRT
<213> ORGANISM: Artificial Sequence
<220> FEATURE:
<223> OTHER INFORMATION: Synthetic Construct

<400> SEQUENCE: 1

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 2
<211> LENGTH: 27
<212> TYPE: PRT
<213> ORGANISM: Artificial Sequence
<220> FEATURE:
<223> OTHER INFORMATION: Synthetic Construct

<400> SEQUENCE: 2

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25
```